United States Patent [19]

Schwenk et al.

[11] 4,219,681
[45] Aug. 26, 1980

[54] PROCESS FOR THE MANUFACTURE OF 2-(PERFLUOROALKYL)-ETHANOLS

[75] Inventors: Ulrich Schwenk, Burghausen; Inge König, Mühldorf; Horst Streitberger, Altötting, all of Fed. Rep. of Germany

[73] Assignee: Hoechst Aktiengesellschaft, Fed. Rep. of Germany

[21] Appl. No.: 64,015

[22] Filed: Aug. 6, 1979

[30] Foreign Application Priority Data

Aug. 9, 1978 [DE] Fed. Rep. of Germany ....... 2834795

[51] Int. Cl.$^2$ ............................................. C07C 31/34
[52] U.S. Cl. .................................. 568/842; 260/653.5
[58] Field of Search .......................................... 568/842

[56] References Cited

U.S. PATENT DOCUMENTS 4,001,309  1/1977  Hayoshi et al. ...................... 568/842

*Primary Examiner*—Howard T. Mars
*Attorney, Agent, or Firm*—Connolly and Hutz

[57] ABSTRACT

2-(perfluoroalkyl)-ethanols of the formula $$R_fCH_2CH_2OH$$

in which $R_f$ is a perfluoroalkyl radical having from 1 to 21 carbon atoms, are prepared in an advantageous manner from the corresponding 2-(perfluoroalkyl)-ethyl iodides by reaction with water and N-methyl-2-pyrrolidone, thus reducing formation of by-products.

5 Claims, No Drawings

PROCESS FOR THE MANUFACTURE OF 2-(PERFLUOROALKYL)-ETHANOLS

The invention relates to a process for the manufacture of 2-(perfluoroalkyl)-ethanols (hereinafter called $R_f$ethanols) of the formula $$R_fCH_2CH_2OH$$

in which $R_f$ is a perfluoroalkyl radical having from 1 to 21 carbon atoms and being linear or branched with methyl in terminal position.

Various processes are known for preparing $R_f$ethanols from the corresponding 2-(perfluoroalkyl)-ethyl iodides (hereinafter called $R_f$ ethyl iodides). These known processes, however, are complicated and expensive, because the intended $R_f$ ethanols cannot be obtained but in a series of process steps.

Thus, according to U.S. Pat. No. 3,246,030, the $R_f$ ethyl iodides are first converted to the corresponding nitrates, from which $R_f$ethanols are obtained by reductive splitting, for example with lithium-aluminum hydride.

According to German Pat. No. 1,214,660, $R_f$ ethyl iodides are reacted with oleum to form the corresponding sulfuric acid esters, which are subsequently hydrolysed to yield the $R_f$ethanols.

According to the process of German Offenlegungsschrift No. 2 318 941, the reaction of $R_f$ ethyl iodides with amides of the formula RCONR'R", in which R, R' and R" each are a hydrogen atom or a lower alkyl radical, and water yields mixtures of $R_f$ethanols, 2-(perfluoroalkyl)-ethyl esters ($R_f$ethyl esters, esterified with the acid on which the amide used is based), and 2-(perfluoroalkyl)-ethylenes ($R_f$ethylenes). The $R_f$ ethyl esters must then be converted to $R_f$ethanols by saponification or transesterification. Further by-products are obtained in addition, some of which, being hydrosoluble, can be eliminated by washing with water. This is however not valid for the 2-(perfluoroalkyl)-ethylamines ($R_f$ethylamines) formed in an amount of up to 5 weight %, which are disturbing for certain applications of the $R_f$ ethanols and therefore must be eliminated, which elimination cannot be performed by distillation in the case of mixtures comprising perfluoroalkyl radicals of different chain length, but must be carried out in a complicated manner, for example via ion exchangers or the intermediate formation of the hydrochlorides. Moreover, the free formic acid which is formed when using dimethyl formamide causes apparatus problems, owing to its corrosive properties, and distillation recovery of dimethyl formamide is handicapped by formation of an azeotropic mixture with formic acid.

It is therefore the object of the present invention to provide a process which allows to obtain the intended $R_f$ethanols in an economic manner with high yield and without substantial amounts of disturbing by-products.

In accordance with the invention, this object is achieved by reacting 2-(perfluoroalkyl)-ethyl iodides of the formula $$R_fCH_2CH_2I$$

in which $R_f$ is as defined above, with water and N-methyl-2-pyrrolidone at a temperature of from 100° to 200° C.

The process of the invention ensures a practically complete conversion of the $R_f$ ethyl iodides, and that the intended $R_f$ ethanols are obtained with high yield (85% and more, relative to $R_f$ ethyl iodide used). $R_f$ ethyl esters are not formed at all. Basic, nitrogen-containing compounds are formed in insignificant amounts only and can be eliminated by washing with water, so that nitrogen-containing reaction products cannot be detected any more in the distilled $R_f$ethanols.

The $R_f$ ethyl iodides used as starting material are easily obtainable by the known telomerization reaction of perfluoroalkyl iodides with ethylene. The perfluoroalkyl iodides may be pure compounds or mixtures of such iodides with perfluoroalkyl iodides of different chain length, which latter ones are obtained by telomerization of shortchain perfluoroalkyl iodides with tetrafluoroethylene; the starting substance optionally being separated from the mixture formed. For practical and economic reasons, preferably those mixtures are telomerized with ethylene, and accordingly, the mixed-chain $R_f$ethyl iodides so obtained are directly used as starting material for the process of the invention.

The starting $R_f$ethyl iodides correspond therefore to the formula $$R_f'(C_2F_4)_nC_2H_4I$$

in which $R_f'$ is perfluoromethyl, perfluoro-n-propyl, preferably perfluoroethyl or perfluoroisopropyl, and n is an integer, or in the case of mixtures optionally a fraction (numerical average), of from 0 to 9.

The molar ratio of water to iodide should be at least 1:1, as well as that of methylpyrrolidone to iodide. When the amount of water is too low, conversion of the iodides is not complete, and in the case of a too large amount of water, the selectivity of the reaction may be reduced. Therefore, a molar ratio of from 1:1 to 10:1, preferably 2:1 to 8:1 is generally chosen.

Advantageously, N-methyl-2-pyrrolidone is employed in excess, and therefore, the molar ratio of N-methyl-2-pyrrolidone to iodide is preferably in the range of from 2:1 to 50:1, especially 5:1 to 25:1. Larger amounts of N-methyl-2-pyrrolidone can be used, but do not bring about any further advantage.

The process of the invention is carried out at temperatures of from 100° to 200° C., preferably 120° to 160° C. At these temperatures, the reaction is complete after about 8 to 14 hours. Advantageously, the reaction is performed at boiling temperature of the starting mixture, which temperature depends on the composition of the $R_f$ethyl iodides and the molar ratio of the reactants.

The reaction is carried out either at normal or at elevated pressure, and advantageously the reactants are intensely intermixed by agitation, by shaking or by other mixing methods.

By addition of water to the reaction mixture, the $R_f$ ethanols obtained are separated as lower phase together with the $R_f$ ethylenes formed as by-products, which lower phase is optionally washed several times with water.

The $R_f$ethylenes are preferably separated from the lower phase by azeotropic distillation with the use of an alkanol having from 1 to 8 carbon atoms, or a monoalkyl ether of ethyleneglycol as entrainer, as described in German Offenlegungsschrift No. 28 32 532. Subsequently, the $R_f$ ethanols are distilled under reduced pressure.

The $R_f$ethanols obtained according to the invention are interesting intermediate products for the manufacture of hydrophobizing, oleophobizing and/or soilrepellent textile finishing agents. For example, the corresponding esters with unsaturated carboxylic acids, such as acrylic or methacrylic acid, can be obtained from these $R_f$ ethanols, from which esters technically important products especially in the field of textile finishing may be prepared by polymerization.

The following examples illustrate the invention.

EXAMPLE 1:

272 g (0.5 mol) of $R_f$ ethyl iodides having the following chain distribution

| | | | |
|---|---|---|---|
| $C_6F_{13}C_2H_4I$ | 49.3% | $C_{10}F_{21}C_2H_4I$ | 12.8% |
| $C_8F_{17}C_2H_4I$ | 32.8% | $C_{12}F_{25}C_2H_4I$ | 5.1% |

27 g (1.5 mols) of water and 1.098 g (11 mols) of N-methyl-2-pyrrolidone are introduced into a 2 liter flask provided with agitator and thermometer, and this mixture is heated with agitation at 150° C. for 13 hours. 2 liters of water are then added to the reaction mixture formed, whereby two phases develop. The lower phase is washed twice for 15 minutes at 70° C. with 500 ml each of water.

The conversion rate $R_f$ ethyl iodide is 100% (determination of the residual iodine content with silver nitrate below the detection limit). Gas chromatography analysis shows 91% of $R_f$ ethanols and 9% of $R_f$ ethylenes.

After addition of 500 ml of methanol to the mixture, the methanol containing $R_f$ ethylenes is distilled off via a 30 cm column up to a bottom temperature of 120° C. By adding water to the distillate the $R_f$ ethylenes separate as lower phase. The remaining contents of the flask are further distilled without column (b.p. at 12 mm Hg: 70° to 147° C.). The residue is 3%. Gas chromatography of the distillate has the following result:

| | |
|---|---|
| $R_f$—$C_2H_4OH$ | 99.2% |
| $R_f$—CH = $CH_2$ | 0.8% |

The chain distribution corresponds to that of the starting $R_f$ ethyl iodide.

EXAMPLE 2:

The apparatus as described in Example 1 is used. A mixture of

| | | |
|---|---|---|
| 237 g | $C_6F_{13}CH_2CH_2I$ | 0.5 mol |
| 1089 g | N-methyl-2-pyrrolidone | 11.0 mol |
| 27 g | $H_2O$ | 1.5 mol | is stirred for 14 hours at 140° C. 1 liter of water is added to the reaction mixture in order to separate the phases. The lower phase is washed twice for 15 minutes at 70° C. with 500 ml each of water. Gas chromatography analysis of this lower phase proves the complete conversion of the iodide. After addition of 500 ml of methanol to the washed lower phase and azeotropic distillation of methanol and $C_6F_{13}CH=CH_2$ as described in Example 1, $C_6F_{13}CH_2CH_2OH$ remains as residue which is further distilled without column, whereby the $R_f$ ethanol passes over: b.p. 12 mm Hg: 76° C. Amount 160.5 g=0.44 mol=88% of yield. A residue of 5.5 g=0.045 mol=3% remains which according to elementary analysis contains no nitrogen. By precipitation with water, 15.6 g of $C_6F_{13}CH=CH_2=0.045$ mol=9%, relative to $R_f$ ethyl iodide used, are obtained from the methanol distillate. Gas chromatography analysis of the alcohol fraction has the following result:

| | |
|---|---|
| 99.8% | $C_6F_{13}CH_2CH_2OH$ |
| 0.2% | $C_6F_{13}CH = CH_2$. |

EXAMPLE 3:

A mixture of 545 g of $R_fCH_2CH_2I$ (1.0 mol) having the following composition

| | |
|---|---|
| $C_6F_{13}CH_2CH_2I$ | 42.3% |
| $C_8F_{17}CH_2CH_2I$ | 34.2% |
| $C_{10}F_{21}CH_2CH_2I$ | 17.5% |
| $C_{12}F_{25}CH_2CH_2I$ | 6.0%, |

594 g of N-methyl-2-pyrrolidone (6.0 mols) and 72 g of water (4.0 mol) is introduced into a 4 liter flask provided with agitator, thermometer and a 30 cm distillation column, and heated with agitation up to 142° C. for 20 hours. Care has to be taken that the low-boiling portion of the reaction mixture is thoroughly refluxed at the head of the column. 1 liter of water is added to the reaction mixture so obtained, and the whole is agitated for 1 hour at 70° C. After having switched off the agitator, 520 g of crude mixture separate after a short time as lower phase.

After washing twice with water at 70° C., the reaction mixture so purified amounts to 438 g and is composed as follows (according to gas chromatography):

| | |
|---|---|
| $R_f$—CH = $CH_2$ | 6.1% |
| $R_f$—$CH_2CH_2OH$ | 93.9% |

After addition of 500 ml of methylglycol, the azeotropic mixture of $R_f$ olefin/methylglycol is distilled off via a mirror glass column up to a bottom temperature of 140° C. The crude alcohol remaining is distilled via a Claisen flask (without column) at 16 mm Hg in a temperature range of from 70° to 147° C. 7 g remain as residue. The distilled $R_f$ ethanol amounting to 397.6 g has the following composition according to gas chromatography:

| | |
|---|---|
| $R_fCH = CH_2$ | 0.3% |
| $R_fCH_2CH_2OH$ | 99.7% |

The chain distribution of $R_fCH_2CH_2OH$ corresponds to the starting $R_f$ ethyl iodide.

What is claimed is:

1. A process for the manufacture of 2-(perfluoroalkyl)ethanols of the formula $R_fCH_2CH_2OH$ wherein
$R_f$ is a linear or terminally methyl-branched perfluoroalkyl having from 1 to 21 carbon atoms from the corresponding 2-(perfluoroalkyl)-ethyl iodides, which comprises reacting these iodides with water and N-methyl-2-pyrrolidone at a temperature in the range of from 100° to 200° C.

2. The process as claimed in claim 1, wherein the molar ratio of water to 2-(perfluoroalkyl)-ethyl iodide is at least 1:1.

3. The process as claimed in claim 1, wherein the molar ratio of water to 2-(perfluoroalkyl)-ethyl iodide is from 1:1 to 10:1.

4. The process as claimed in claim 1, wherein the molar ratio of N-methyl-2-pyrrolidone to 2-(perfluoroalkyl)-ethyl iodide is at least 1:1.

5. The process as claimed in claim 1, wherein the molar ratio of N-methyl-2-pyrrolidone to 2-(perfluoroalkyl)-ethyl iodide is from 2:1 to 50:1.

* * * * *